(12) United States Patent
Iyappan et al.

(10) Patent No.: US 9,752,170 B2
(45) Date of Patent: Sep. 5, 2017

(54) METHOD OF PRODUCTION OF MONOSACCHARIDES

(71) Applicant: Petiva Private Limited, Hyderabad, Telangana (IN)

(72) Inventors: Saravanakumar Iyappan, Telangana (IN); Samir Kumar Roy, Telangana (IN); Saju Varghese, Telangana (IN); Aparna Devi Addala, Telangana (IN); Venkata Narayanan Karthikeyan, Telangana (IN); Kanumuru Rahul Raju, Telangana (IN); Banibrata Pandey, Telangana (IN)

(73) Assignee: Petiva Private Limited, Hyderabad, Telangana (IN)

( * ) Notice: Subject to any disclaimer, the term of this patent is extended or adjusted under 35 U.S.C. 154(b) by 47 days.

(21) Appl. No.: 14/655,034

(22) PCT Filed: Apr. 17, 2013

(86) PCT No.: PCT/IB2013/053038
§ 371 (c)(1),
(2) Date: Jun. 23, 2015

(87) PCT Pub. No.: WO2013/156939
PCT Pub. Date: Oct. 24, 2013

(65) Prior Publication Data
US 2015/0361473 A1    Dec. 17, 2015

(30) Foreign Application Priority Data

Apr. 17, 2012 (IN) .......................... 1539/DEL/2012

(51) Int. Cl.
*C12P 19/24* (2006.01)
*C12N 9/90* (2006.01)
*C12P 19/02* (2006.01)

(52) U.S. Cl.
CPC ............... *C12P 19/24* (2013.01); *C12N 9/90* (2013.01); *C12P 19/02* (2013.01); *C12Y 501/03* (2013.01); *C12Y 503/01014* (2013.01)

(58) Field of Classification Search
CPC .................................. C12P 19/24; C12N 9/90
USPC .................. 435/233, 252.3, 320.1; 536/23.2
See application file for complete search history.

(56) References Cited

U.S. PATENT DOCUMENTS

| 5,679,562 A | 10/1997 | Izumori et al. |
| 5,811,271 A | 9/1998 | Izumori et al. |

FOREIGN PATENT DOCUMENTS

| EP | 1589102 A1 | 10/2005 |
| WO | WO03061603 A2 | 7/2003 |
| WO | WO2004050877 A1 | 6/2004 |

OTHER PUBLICATIONS

Ishida et al., Cloning and characterization of the d-tagatose 3-epimerase gene from Pseudomonas cichorii ST-24, Journal of Fermentation and Bioengineering (1997), 83(6):529-534.
Tekeshita et al., Mass production of D-psicose from d-fructose by a continuous bioreactor system using immobilized D-tagatose 3-epimerase, J Biosci Bioeng (2000), 90(4):453-455.
Yoshida et al., Crystal structures of D-tagatose 3-epimerase from Pseudomonas cichorii and its complexes with D-tagatose and D-fructose, J Mol Biol (2007), 74(2):443-453.
Ishida et al., Production of d-tagatose 3-epimerase of Pseudomonas cichorii ST-24 using recombinant *Escherichia coli*, Journal of Fermentation and Bioengineering (1997), 84(4):348-350.
Leang et al., Cloning, nucleotide sequence, and overexpression of the L-rhamnose isomerase gene from Pseudomonas stutzeri in *Escherichia coli*, Appl Environ Microbiol (2004), 70(6):3298-3304.
Madduri et al., Rhamnose Biosynthesis Pathway Supplies Precursors for Primary and Secondary Metabolism in Saccharopolyspora spinosa, J Bacteriol (2001), 183(19):5632-5638.

*Primary Examiner* — Tekchand Saidha
(74) *Attorney, Agent, or Firm* — Bret E. Field; Bozicevic, Field & Francis LLP

(57) ABSTRACT

The present invention is directed towards genetic modification of native gene encoding for D-tagatose 3-epimerase and rhamnose isomerase to substantially increase the expression level of these enzymes and use of the enzymes in a process to produce rare monosaccharides such as psicose and allose. Also disclosed in the present invention is expression constructs comprising the modified genes and a host cells to express the same.

13 Claims, 14 Drawing Sheets

Figure 1: Schematic view of a gene construct generated for expression of D-tagatose 3-epimerase in *E. coli*
A
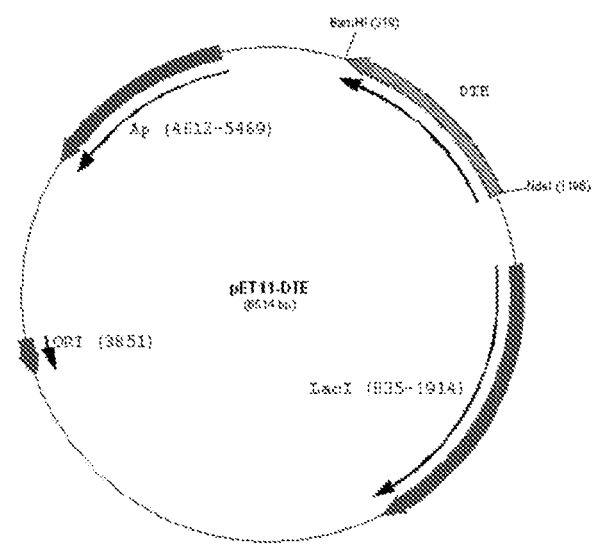
B
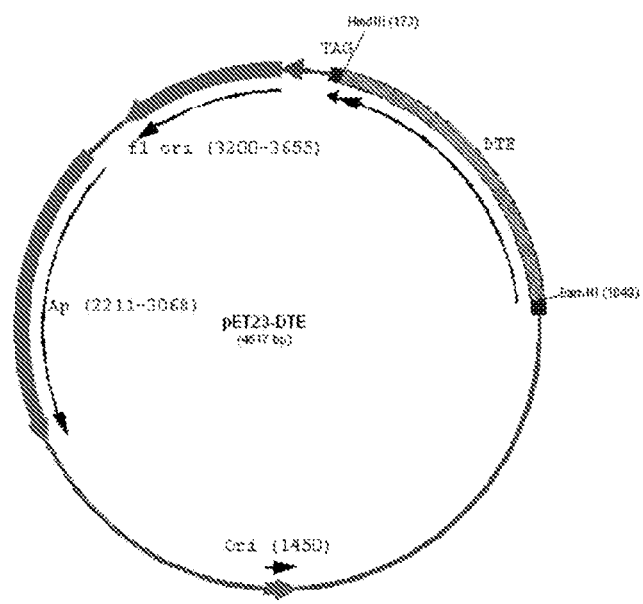

Figure 2: Schematic view of a gene construct generated for expression of rhamnose isomerase in *E. coli*
A
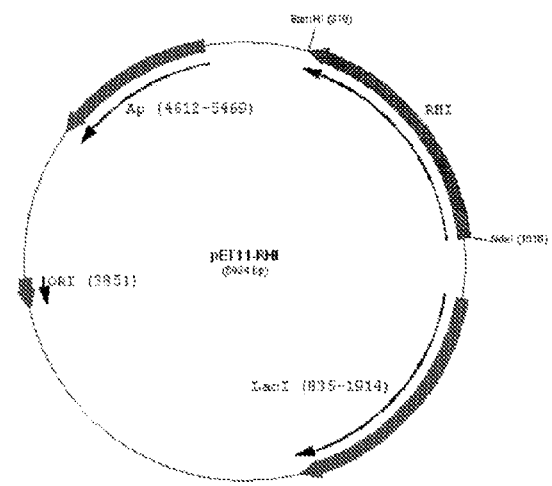
B
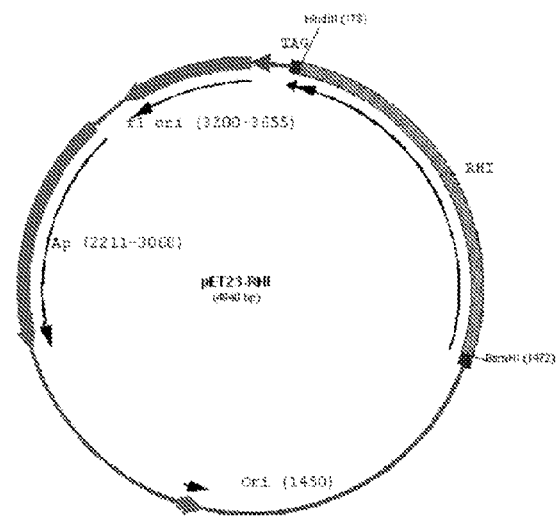

Figure 3: Expression analysis of recombinant D-tagatose 3-epimerase in *E. coli*.
A
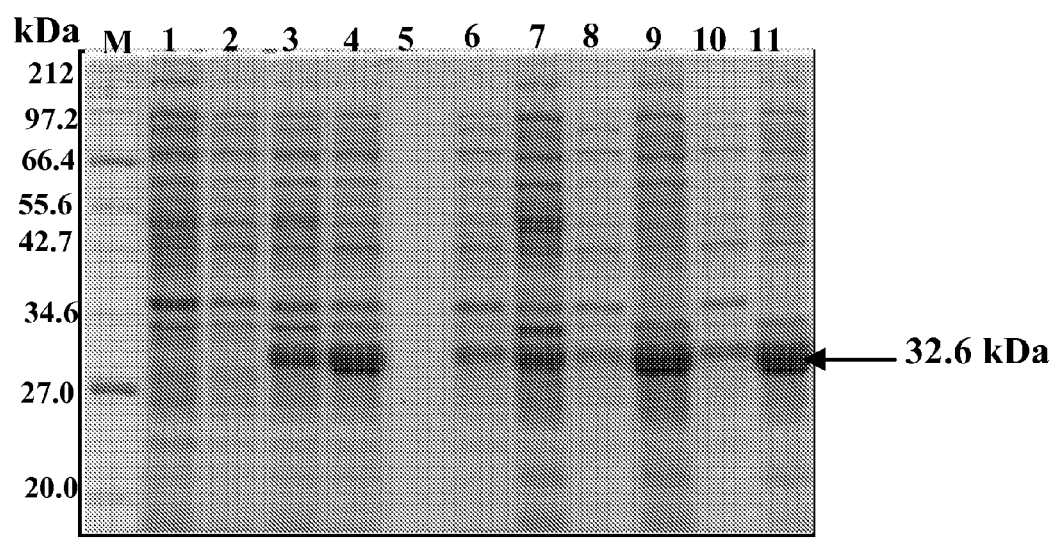
B
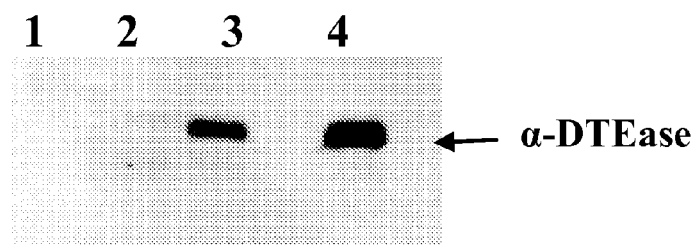

Figure 4: Expression analysis of recombinant rhamnose isomerase in *E. coli*.
A
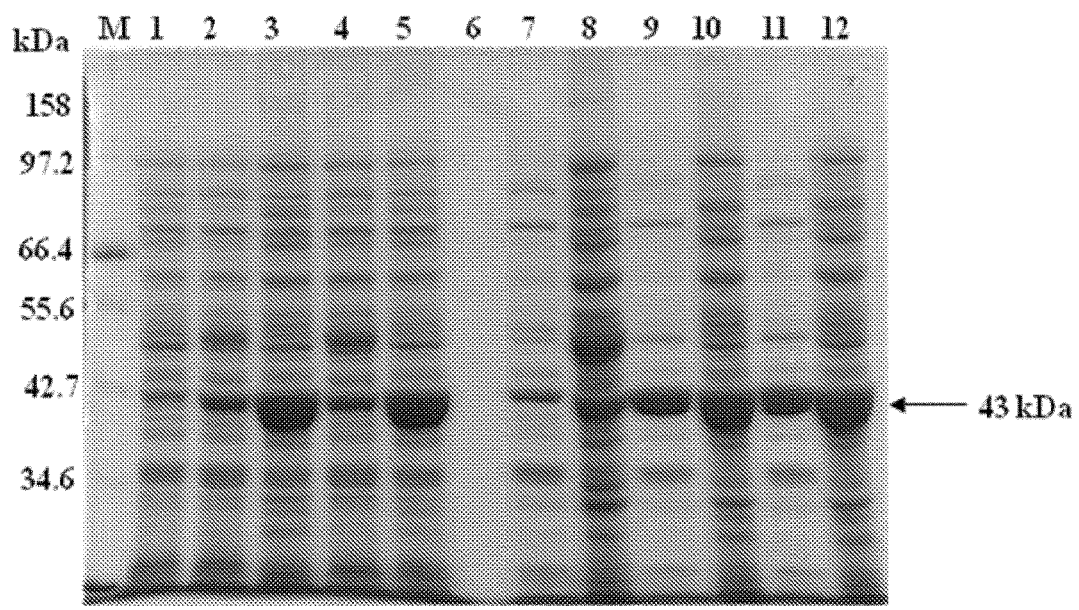
B
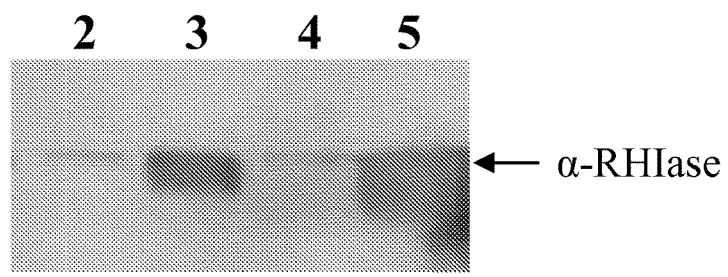

Figure 5: HPLC analysis of recombinant D-tagatose 3-epimerase activity for substrate to product conversion.
A
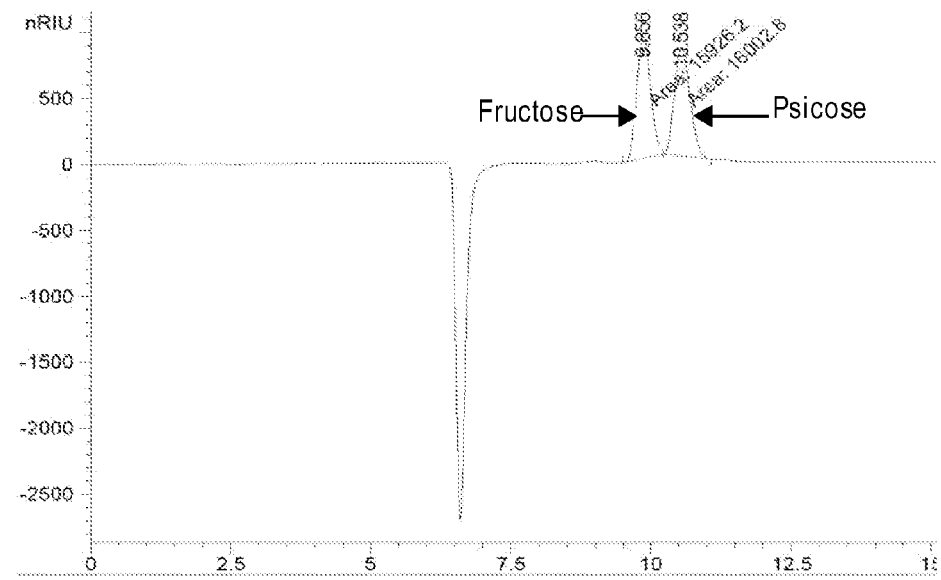
B
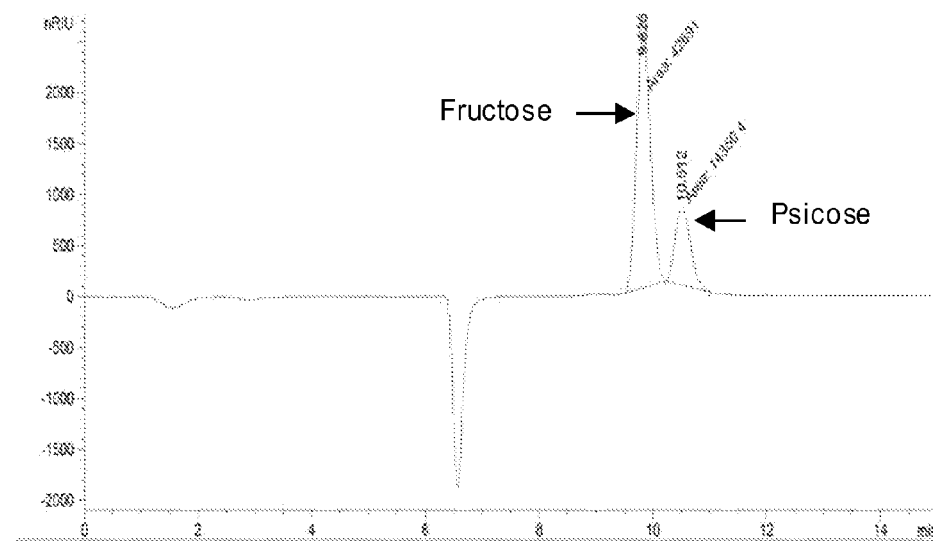

Figure 6: HPLC analysis of recombinant rhamnose isomerase activity for substrate to product conversion.
A
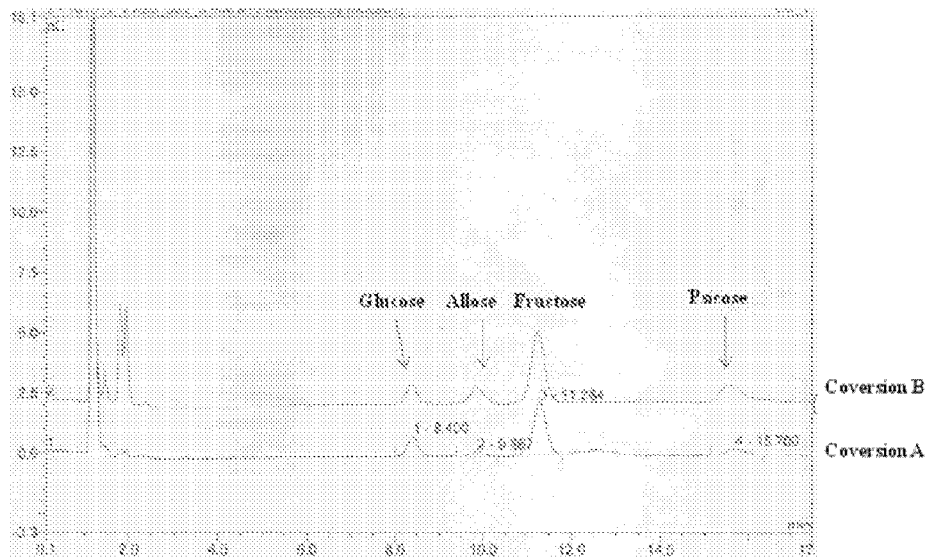
B
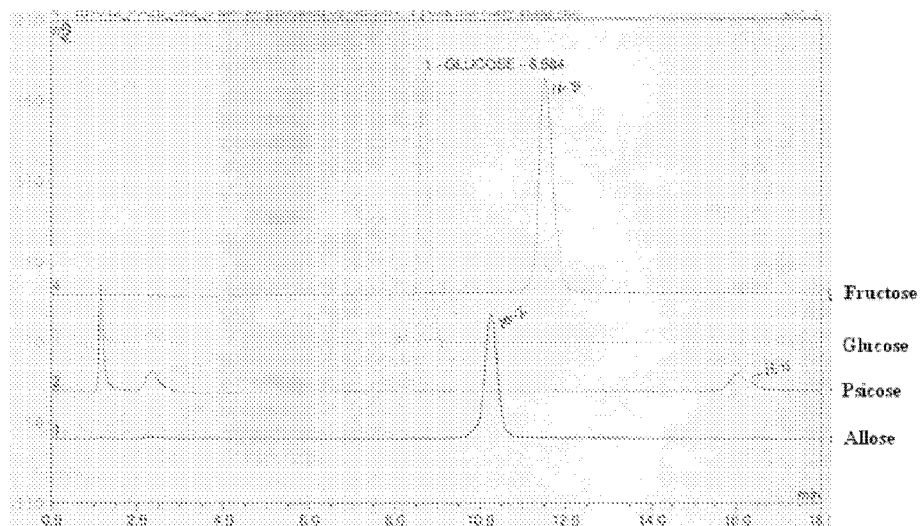

Figure 7: Analysis of purified DTEase
A
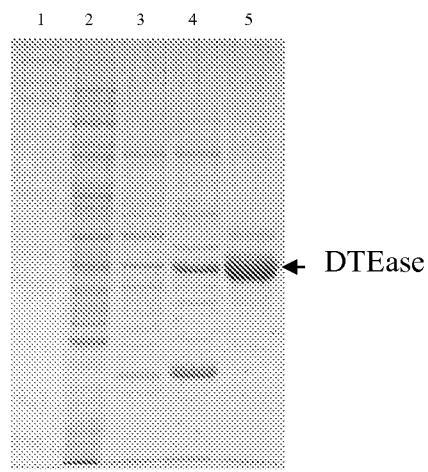
B
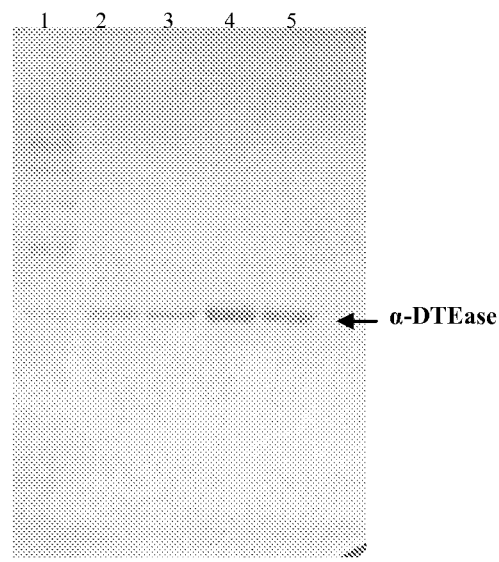

Figure 8: Analysis of purified RHIase
A
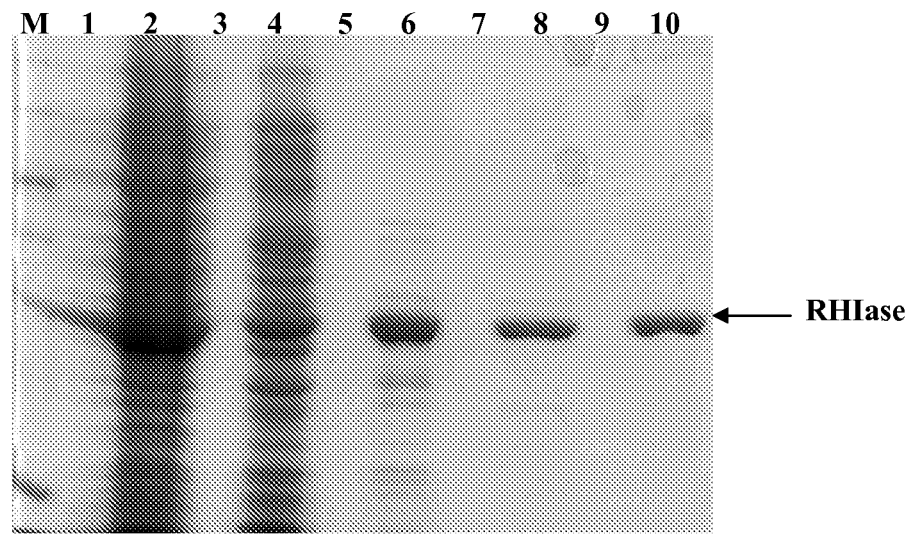
B
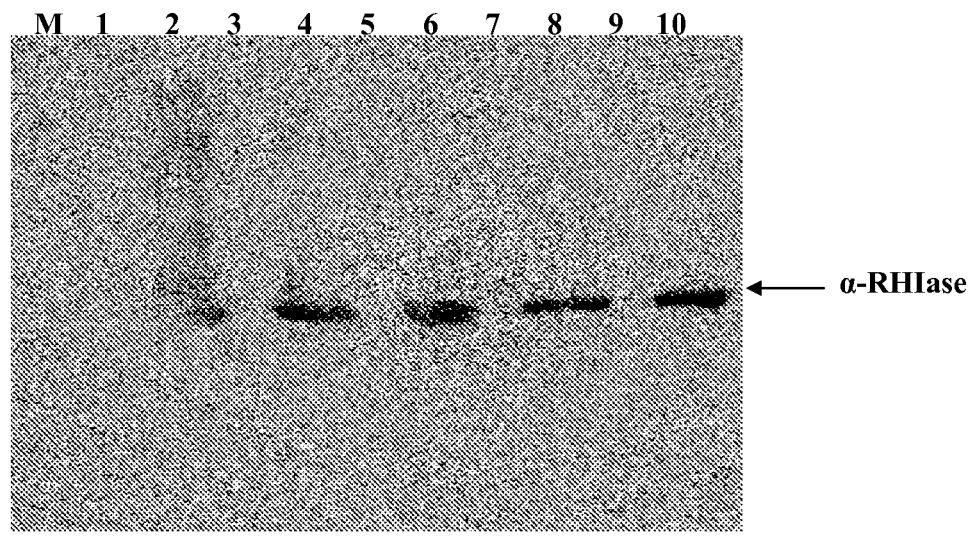

Figure 9: Activity of a D-tagatose 3-epimerase against reaction pH and reaction temperature
A
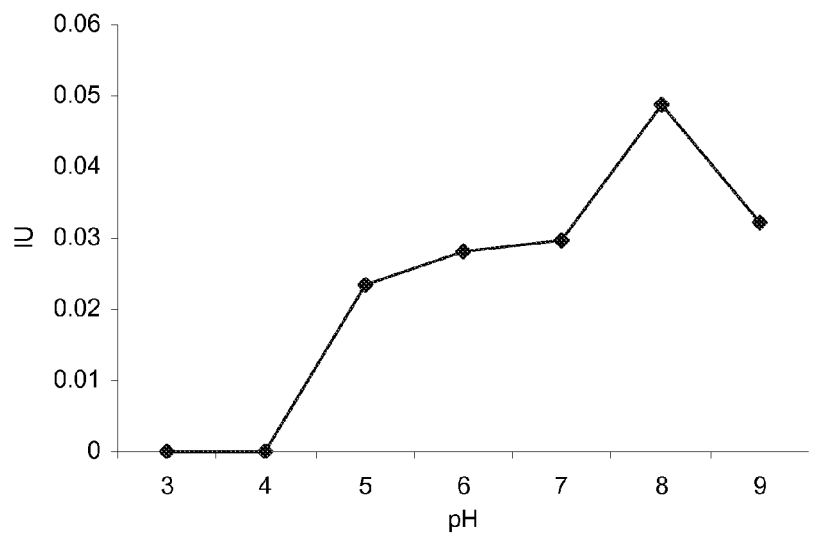
B
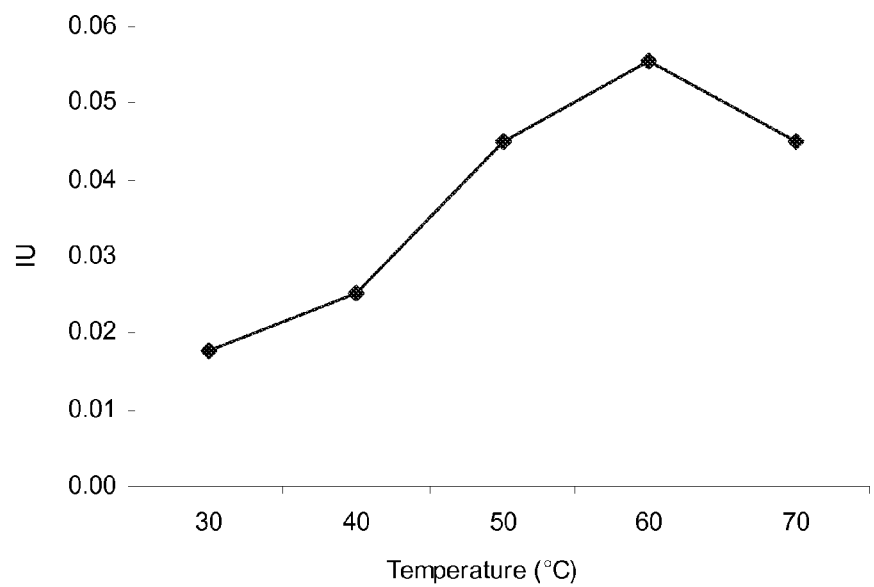

Figure 10: Activity of a rhamnose isomerase against reaction pH and reaction temperature.
A.
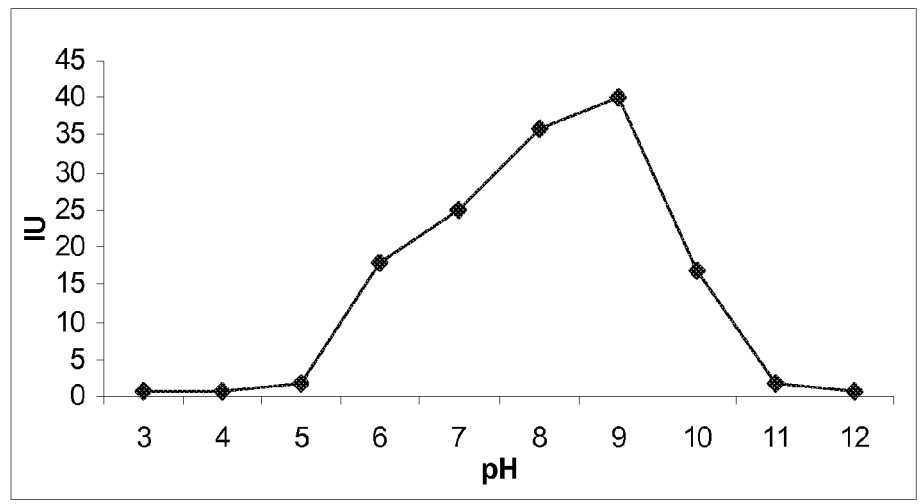
B.
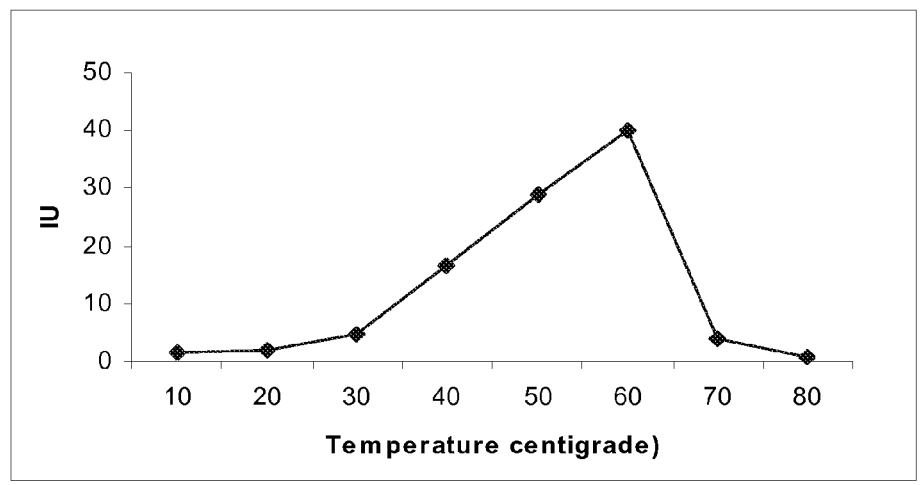

Figure 11: Sequence alignment analysis of modified gene sequence encoding for D-tagatose 3-epimerase with native gene sequence of *Pseudomonas cichorii* ST-24.

```
Modified    ATGAATAAAGTGGGCATGTTCTACACGTACTGGAGCACCGAATGGATGGTTGATTTTCCG 60
Native      GTGAACAAAGTTGGCATGTTCTACACCTACTGGTCGACTGAGTGGATGGTCGACTTTCCG 60
            .****.*****.***************.******....**.**.********.**.******

Modified    GCGACGGCTAAACGCATTGCAGGTCTGGGCTTTGATCTGATGGAAATTCTCTGGGTGAA 120
Native      GCGACTGCCAAGCGCATTGCCCGGCTCGGCTTCGACTTAATGGAAATCTCGCTCGCCGAG 120
            *****.**.**.********.**.**.*****.**..*.********.**.**.**.**.

Modified    TTCCATAACCTGAGTGATGCGAAAAAACGTGAACTGAAAGCGGTTGCCGATGATCTGGGC 180
Native      TTTCACAATCTTTCCGACGCGAAGAAGCGTGAGCTAAAAGCCGTGGCTGATGATCTGGGG 180
            **.**.**.**....**.*****.**.*****.**.*****.**.**.***********.

Modified    CTGACCGTGATGTGCTGTATCGGTCTGAAATCTGAATATGATTTTGCGAGTCCGGATAAA 240
Native      CTCACGGTGATGTGCTGTATCGGACTGAAGTCTGAGTACGACTTTGCCTCGCCGGACAAG 240
            **.**.******************.****.*****.**.**.*****....*****.**.

Modified    AGCGTTCGTGATGCCGGCACCGAATACGTGAAACGCCTGCTGGATGATTGCCACCTGCTG 300
Native      AGCCTTCCTCATCCCGGCACCGAATATGTCAAGCCCTTGCTCCACCACTCTCACCTCCTC 300
            ****.***.*.**.**.************.****.***.**.**.**.**.**.*****.**.

Modified    GGCGCACCGGTTTTTGCGGGTCTGACGTTCTGTGCATGGCCGCAGAGCCCGCCGCTGGAT 360
Native      GGCGCGCCGGTCTTTGCTGGCCTTACGTTCTGCGCGTGGCCCCAATCTCCGCCGCTGGAC 360
            *****.*****.*****.**.**.********.**.*****....***.***********.

Modified    ATGAAAGATAAACGTCCCTATGTGGATCGCGCCATTGAATCTGTCCGTCGCGTTATCAAA 420
Native      ATGAAGGATAAGCGCCCTTACGTCGACCGTGCAATCGAAAGCGTTCGTCGTGTTATCAAG 420
            *****.*****.**.**.**.**.**.**.**.**.****.....*******.*******.

Modified    GTGGCCGAAGATTATGGTATTATCTACGCACTGGAAGTGGTTAACCGTTTTGAACAGTGG 480
Native      GTAGCTGAAGACTACGGCATTATTTATGCACTGGAAGTGGTGAACCGATTCGAGCAGTGG 480
            **.**.*****.**.**.**.**.*****.***************.*****.**.**.******

Modified    CTGTGCAATGATGCCAAAGAAGCAATTGCGTTCGCCGATGCAGTTGATAGTCCGGCATGT 540
Native      CTTTGCAATGACGCCAAGGAAGCAATTGCGTTTGCCGACGCGGTTGACAGTCCGGCGTGC 540
            **.********.*****.************.*****.**.*****.**.*******.**.

Modified    AAACTGCAGCTGCATACCTTTCATATCAACATTGAACAAACCAGCTTCCGCCATGCCATC 600
Native      AAGGTCCAGCTCGACACATTCCACATGAATATCGAAGAGACTTCCTTCCGCGATGCAATC 600
            **.**.*****.**.**.**.**.**.*****.**.*****.**....***********.***

Modified    CTGGCCTGCAAAGGCAAAATGGGTCATTTCCACCTGGGTCAAGCAAATCGTCTGCCGCCG 660
Native      CTTGCCTGCAAGGGCAAGATGGGCCATTTCCATTTGGGCGAAGCGAACCGTCTGCCGCCG 660
            **.********.*****.******.********.*****.*****.**.***********

Modified    GGTGAAGGTCGTCTGCCGTGGGATGAAATCTTTGGTGCCCTGAAAGAAATTGGCTACGAT 720
Native      GGCGAGGGTCGCCTGCCGTGGGATGAAATATTCGGGGCGCTGAAGGAAATCGGATATGAC 720
            **.**.*****.*****************.**.**.**.*****.*****.**.**.**.

Modified    GGTACCATCGTTATGGAACCGTTCATGCGCAAAGGCGGTAGCGTGTCTCGTGCAGTGGGC 780
Native      GGCACCATCGTTATGGAACCGTTCATGCGCAAGGGCGGCTCGGTCAGCCGCGCGGTGGGC 780
            **.************************.****....**....**.**.**.********

Modified    GTTTGGCGCGATATGAGCAATGGTGCGACGGATGAAGAAATGGATGAACGTGCTCGTCGT 840
Native      GTATGGCGGGATATGTCGAACGGTGCGACGGACGAAGAGATGGACGAGCGCGCTCGCCGC 840
            **.*****.******....**.**********.*****.*****.**.**.*****.**.

Modified    AGCCTGCAATTCGTGCGTGATAAACTGGCGTAA 873
Native      TCGTTGCAGTTTGTTCGTGACAAGCTGGCCTGA 873
            ....****.**.**.*****.**.*****.*.*
```

Figure 12: Sequence alignment analysis of modified gene sequence encoding for rhamnose isomerase with native gene sequence of *Pseudomonas stutzeri*.

Figure 12 (cont.)

```
Modified    CATCCGCCCACATGATTGATCAGAGCCACAACGTTACCGATCCGATGAATCCTGATC   1020
Native      CACCCCGCCCACATGATCGACCAGCCCACAACGTCACCGACCCCATCGAGGCCGATC   1020
            ** ** ***** ***** ** ** *** **** ** ****  ** **** ** ****

Modified    AACAGTGCGAATGAAATCCCTGGCCGGATGGCAGGCACTGCTGGTTGATCCCCAGCC   1080
Native      AACAGCGCCGAACGAAATTCCCTGTCTATGGCAGGCCGCCGGTCGACCCCCAGCCC   1080
            ***** ** *** ***** ** *  ***** *****  ** ** ** ******

Modified    CTGCTGGTTACCAGGAAGATAACGATCCCCTGATCGCCATCGAAGATGAAACGCGGCA   1140
Native      CTTTTGGTCACCAGGAGGACAACGACCCCCTGATCGCGATCGAAGTTGAAGCGCGCC   1140
            ** ** ** ****** ** ***** ********* ** ******  *** ** **

Modified    TATCGTACCCGATGTGGAACTGATTTGTCGAGCAGCGCGGGGACGGGCCGGCTAGTG   1200
Native      TACCGTACCGATGTTGAGTTGATTCTGCGAGCGGGCGGCGCCCACGGGCGCCTGTG   1200
            ** ****** *** ***  ***** ** **** ** **  ** ****** ** **

Modified    GATTTTTTGCAACCTACCGGCCCAGCGGGCTATCGTCTTTGTGTGCGGCGAACCTCCG   1260
Native      GACCTCGTCGCGACCTATCCGGACAGCCCCTACCCGTCAGGGTCGCCGCTGAGCGCC   1260
            **  **  **  ***** ***  *** ** **  **** ** ** ** ** ** **

Modified    CCATCAGTTACGGGTGGTGGCGGTATTATCTAA   1293
Native      CCCTCGCTGACGGGTGGGGACGGCATCATCTGA   1293
            **  **    ******* * ** ** *****
```

Table 1: Purification table D-tagatose 3-epimerase

| Steps | Sample | Volume (ml) | Protein (mg/ml) | Total protein (mg) | Specific activity (IU/mg) | Total activity (IU) | Protein yield (%) | Fold of purification | Activity recovery (%) |
|---|---|---|---|---|---|---|---|---|---|
| First purification | Loading | 215.0 | 13.0 | 2793 | 0.95 | 2635 | 100 | 1.0 | 100 |
| | Pooled fractions | 80.0 | 5.0 | 404 | 5.50 | 2245 | 14.50 | 6.90 | 85.2 |
| Second purification | Pooled fractions | 63.0 | 3.0 | 195 | 10.30 | 2022 | 6.98 | 11.00 | 76.7 |

Table 2: Purification table for rhamnose isomerase

| Steps | Sample | Volume (ml) | Protein (mg/ml) | Total protein (mg) | Specific activity (IU/mg) | Total activity (IU) | Protein yield (%) | Fold of purification | Activity recovery (%) |
|---|---|---|---|---|---|---|---|---|---|
| Cell lysate | Loading | 60 | 6 | 360 | 0.997 | 359 | 100 | 1 | 100 |
| Purification | Pooled fractions | 50 | 0.936 | 46.8 | 5.83 | 273.31 | 13 | 7.69 | 76 |

Figure 12 (cont.)

Table 3: Production of D-Psicose by immobilized recombinant D-tagatose 3-epimerase

| Substrate (%) | Immobilized enzyme (IU) | D-psicose : D-fructose ratio after 8 hours of bioconversion |
|---|---|---|
| 10 | 140 | 20.7 : 79.3 |
| 30 | 140 | 21.8 : 78.2 |
| 50 | 140 | 22.7 : 77.3 |
| 70 | 140 | 22.5 : 77.5 |
| 80 | 140 | 20.5 : 79.5 |

Table 4: Production of D-allose by immobilized recombinant rhamose isomerase

| Substrate (%) | Immobilized enzyme (IU) | D-allose : D-psicose ratio after 12 hours of bioconversion |
|---|---|---|
| 10 | 100 | 23.9: 76.1 |
| 30 | 100 | 24.3: 75.7 |
| 50 | 100 | 25.1: 74.9 |
| 70 | 100 | 24.9: 75.1 |
| 80 | 100 | 24.8: 75.2 |

SEQUENCE LISTING

```
<160> NUMBER OF SEQ ID NOS: 4

<210> SEQ ID NO 1
<211> LENGTH: 873
<212> TYPE: DNA
<213> ORGANISM: Artificial Sequence
<220> FEATURE:
<223> OTHER INFORMATION: Modified gene sequence coding for D-tagatose
      3-epimerase of Pseudomonas cichorii ST-24

<400> SEQUENCE: 1
atgaataaag tgggcatgtt ctacacgtac tggagcaccg aatggatggt tgattttccg        60
gcgacggcta aacgcattgc aggtctgggc tttgatctga tggaaatttc tctgggtgaa       120
ttccataacc tgagtgatgc gaaaaaacgt gaactgaaag cggttgccga tgatctgggc       180
ctgaccgtga tgtgctgtat cggtctgaaa tctgaatatg attttgcgag tccggataaa       240
agcgttcgtg atgccggcac cgaatacgtg aaacgcctgc tggatgattg ccacctgctg       300
ggcgcaccgg tttttgcggg tctgacgttc tgtgcatggc cgcagagccc gccgctggat       360
atgaaagata aacgtccgta tgtggatcgc gccattgaat ctgtgcgtcg cgttatcaaa       420
gtggccgaag attatggtat tatctacgca ctggaagtgg ttaaccgttt tgaacagtgg       480
ctgtgcaatg atgccaaaga agcaattgcg ttcgccgatg cagttgatag tccggcatgt       540
aaagtgcagc tggatacctt tcatatgaac attgaagaaa cgagcttccg cgatgcgatc       600
ctggcctgca aaggcaaaat gggtcatttc cacctgggtg aagcaaatcg tctgccgccg       660
ggtgaaggtc gtctgccgtg ggatgaaatc tttggtgccc tgaaagaaat tggctacgat       720
ggtaccatcg ttatggaacc gttcatgcgc aaaggcggta gcgtgtctcg tgcagtgggc       780
gtttggcgcg atatgagcaa tggtgcgacg gatgaagaaa tggatgaacg tgctcgtcgt       840
agcctgcaat tcgtgcgtga taaactggcg taa                                    873

<210> SEQ ID NO 2
<211> LENGTH: 1293
<212> TYPE: DNA
<213> ORGANISM: Artificial Sequence
<220> FEATURE:
<223> OTHER INFORMATION: Modified gene sequence encoding rhamnose
      isomerase of Pseudomonas stutzeri to enhance the expression in
      hetrologus host

<400> SEQUENCE: 2
atggctgaat tccgtatcgc tcaagatgtt gtcgctcgtg aaaatgaccg tcgtgcctcg        60
gctctgaaag aagactatga agcactgggc gcaaatctgg cgcgtcgcgg tgtggatatt       120
gaagccgtga cggcaaaagt tgaaaaattt tcgtggcag ttccgagctg gggtgttggt        180
accggcggta cgcgctttgc acgtttcccg ggtaccggtg aaccgcgtgg tatttttgat       240
aaactggatg attgcgcggt gatccagcag ctgacccgtg ccacgccgaa tgttagtctg       300
catatcccgt gggataaagc ggatccgaaa gaactgaaag cacgtggtga tgcactgggt       360
ctgggttttg atgccatgaa cagtaatacc ttcagcgatg ccccgggcca ggcacatagc       420
```

```
tataaatacg gtagcctgtc tcacaccgat gcagcaacgc gtgcacaggc agtggaacac    480
aacctggaat gtattgaaat cggcaaagca attggttcta aagcgctgac ggtttggatc    540
ggcgatggta gcaactttcc gggccagtct aattttaccc gcgccttcga acgttatctg    600
agtgcgatgg ccgaaattta caaaggcctg ccgatgatt ggaaactgtt tagtgaacat     660
aaaatgtacg aaccggcgtt ctacagcacc gtggttcagg attggggcac gaattatctg    720
atcgcccaga ccctgggtcc gaaagcacag tgcctggtgg atctgggcca tcacgcaccg    780
aacaccaata ttgaaatgat cgttgcgcgc ctgattcagt ttggtaaaact gggcggtttt    840 catttcaacg attctaaata tggcgatgat gatctggatg caggtgcgat cgaaccgtac    900
cgcctgtttc tggtgttcaa tgaactggtt gatgccgaag cacgtggcgt gaaaggtttc    960
catccggccc acatgattga tcagagccac aacgttacgg atccgattga atctctgatc   1020
aacagtgcga atgaaatccg tcgcgcgtat gcccaggcac tgctggttga tcgcgcagcg   1080
ctgtctggtt accaggaaga taacgatgcg ctgatggcca ccgaaacgct gaaacgcgca   1140
tatcgtaccg atgtggaacc gattctggca gaagcacgtc gccgtacggg cggtgcagtg   1200
gatccggttg caacctaccg tgccagcggc tatcgtgctc gtgtggcggc agaacgtccg   1260
gcatcagttg cgggtggtgg cggtattatc taa                                1293

<210> SEQ ID NO 3
<211> LENGTH: 873
<212> TYPE: DNA
<213> ORGANISM: Pseudomonas cichorii

<400> SEQUENCE: 3
gtgaacaaag ttggcatgtt ctacacctac tggtcgactg agtggatggt cgactttccg     60
gcgactgcga agcgcattgc cgggctcggc ttcgacttaa tggaaatctc gctcggcgag    120
tttcacaatc tttccgacgc gaagaagcgt gagctaaaag ccgtggctga tgatctgggg    180
ctcacggtga tgtgctgtat cggactgaag tctgagtacg actttgcctc gccggacaag    240
agcgttcgtg atgccggcac ggaatatgtg aagcgcttgc tcgacgactg tcacctcctc    300
ggcgcgccgg tctttgctgg ccttacgttc tgcgcgtggc cccaatctcc gccgctggac    360
atgaaggata agcgccctta cgtcgaccgt gcaatcgaaa gcgttcgtcg tgttatcaag    420
gtagctgaag actacggcat tatttatgca ctggaagtgg tgaaccgatt cgagcagtgg    480
ctttgcaatg acgccaagga agcaattgcg tttgccgacg cggttgacag tccggcgtgc    540
aaggtccagc tcgacacatt ccacatgaat atcgaagaga cttccttccg cgatgcaatc    600
cttgcctgca agggcaagat gggccatttc catttgggcg aagcgaaccg tctgccgccg    660
ggcgagggtc gcctgccgtg ggatgaaata ttcggggcgc tgaaggaaat cggatatgac    720
ggcaccatcg ttatggaacc gttcatgcgc aagggcggct cggtcagccg cgcggtgggc    780
gtatggcggg atatgtcgaa cggtgcgacg gacgaagaga tggacgagcg cgctcgccgc    840
tcgttgcagt ttgttcgtga caagctggcc tga                                 873

<210> SEQ ID NO 4
<211> LENGTH: 1293
<212> TYPE: DNA
<213> ORGANISM: Pseudomonas stutzeri

<400> SEQUENCE: 4
atggctgaat tcaggatcgc tcaggatgtc gttgcgcggg aaaacgacag gcgcgcctcg     60
```

```
gcgctgaagg aagactacga ggcgctcggc gcgaatctcg cccgccgtgg cgtcgacatc      120
gaggccgtca cggccaaggt cgaaaagttc ttcgtcgccg tcccctcctg gggcgtcggc      180
acgggcggca cgcgctttgc gcgcttcccc ggcaccggcg agccgcgcgg catcttcgac      240
aagctggacg actgcgccgt catccagcag ctgacacgcg ccacgcccaa tgtctcgctg      300
catattccgt gggacaaggc cgatccgaag gagctgaagg ccaggggcga cgccctcggc      360
ctcggcttcg acgcgatgaa ctccaatacc ttctccgatg cgcccggcca ggcgcattcc      420
tacaaatacg gctcgctcag ccacacggat gcggcaacgc gcgcccaggc ggtcgagcac      480
aatctggaat gcatcgagat cggcaaggcc atcggctcca aggcgctgac ggtctggatc      540
ggtgacggct ccaacttccc cggccagagt aacttcacca gggctttcga acgttatctc      600
tcggcgatgg cggagatcta caagggcctg ccggatgact ggaagctgtt ctccgagcac      660
aagatgtacg agccggcctt ctattcgacc gtcgtgcagg actggggcac gaattatctc      720
atcgcccaga cgctcggccc caaggcccag tgcctcgtcg atctcggcca tcacgcgccg      780
aacaccaata tcgagatgat cgtcgcccgg ctcatccagt tcggcaagct cggcggcttc      840
catttcaacg attccaaata cggcgacgac gacctcgatg ccggcgccat cgagccctat      900
cgcctcttcc tcgtcttcaa cgagctggtg gatgcggagg cgcgcggcgt caagggcttc      960
cacccggccc acatgatcga ccagtcgcac aacgtcaccg acccgatcga gagcctgatc      1020
aacagcgcga acgaaatccg tcgcgcctat gcgcaggccc tccttgtcga ccgcgcggcg      1080
ctttccggct accaggagga caacgacgcc ctgatggcga cggaaacgtt gaagcgcgcc      1140
taccgtaccg atgtggagcc gatcctcgcc gaggcccgcc gccgcacggg cggcgccgtc      1200 gacccgtcg cgacctatcg ggccagcggc taccgcgcca gggtcgccgc cgagcgcccc      1260
gcctccgtcg cgggtggcgg cggcatcatc tga                                  1293
```

METHOD OF PRODUCTION OF MONOSACCHARIDES

FIELD OF THE INVENTION

The present invention is in the field of biotechnology and more particularly production of rare sugars through biological route.

BACKGROUND OF THE INVENTION

Despite their low natural abundance, rare sugars hold enormous potential for practical application. Some of the use of the rare sugars ranges from low caloric sweetener to medical application.

Research on rare sugars is progressing rapidly and the application of these rare sugars has been spread quite widely to sweeteners, functional foods, medicines, cosmetics, and surprisingly to agrochemical fields. In addition, rare sugars can be used as starting materials for the synthesis of intriguing natural products with important biological activities. Unfortunately, most rare sugars are quite expensive, and their synthetic routes are both limited and costly due to the expense of costly starting materials.

D-Psicose is one of the important hexose rare sugar useful as low caloric sweetener, anti-oxidant, and as an agrochemical. Psicose, a carbon-3 epimer of Fructose, is a rare monosaccharide. In nature, the Psicose is present as a non-fermentable constituent of cane molasses in a very minute quantity, a sugar moiety of the nucleoside antibiotic psicofuranine, and as free sugar in wheat and itea plants. Psicose has the unique property of being an ideal sucrose substitute as a non-caloric sweetener for weight reduction and a nontoxic sugar.

Compared with sucrose, it has 70% the sweetness but provides no energy due to its suppressive effect toward hepatic lipogenic enzymes. Furthermore, it has been observed that foods supplemented with Psicose exhibit higher antioxidant activity.

Moreover, Psicose can be used as a precursor in the synthesis of xylosylpsicoses, which are promising candidates for prebiotics, cosmetics and therapeutic uses. Allose is another important hexose rare sugars useful as low caloric sweetener. Allose, an aldohexose, is C-3 epimer of D-glucose, exists rarely in nature but has been isolated from the leaves of the African shrub *Protea rubropilosa*. Allose has the unique property of being an ideal sugar substitute as a non-caloric sweetener for weight reduction and a nontoxic sugar. Moreover Allose has beneficial activities, including anti-cancer, anti-tumour, anti-inflammatory, anti-oxidative, anti-hypertensive, cryoprotective, and immunosuppressant activities. Allose is as sweet compared to sucrose but provides no energy due to its suppressive effect toward hepatic lipogenic enzymes.

The enzyme responsible for bioconversion of ketose to its corresponding epimeric ketose (fructose to psicose) form have been reported from different microorganisms such as *Agrobacterium tumefaciens, Rhodobacter Sphaeroides, Ruminococcus* sp, *RHIzobium leguminosarum, Clostridium cellulolyticum* H10 and *Pseudomonas cichorii* ST-24. U.S. Pat. No. 5,679,562 discloses enzyme from *Pseudomonas cichorii* ST-24 having ability to convert ketose sugars to their corresponding epimeric form. U.S. Pat. No. 5,811,271 described the conversion of L-ketohexoses to its epimeric form with the D-ketohexose 3-epimerase and reported the affinity of the enzyme towards tagatose. The same enzyme is sometimes referred as D-tagatose-3-epimerase due its more specificity towards D-tagatose compared to Fructose. Similarly the enzymes responsible for bioconversion of ketose to aldose (Psicose in to Allose) form have been reported from different microorganisms as well such as *Escherichia coli, Salmonella, Pseudomonas* spp and *Thermoanaerobacterium saccharolyticum*. EP 0807682 discloses the ribose isomerase from *Acinetobacter calcoaceticus* LR7C capable of converting L-ribose into L-ribulose and vice versa. EP 1589102 disclosed DNA sequence of L-rhamnose isomerase derived from *Pseudomonas stutzerii*.

The mass production of pure Psicose and Allose is critical to meet the commercial value due to insufficient production of enzyme as biocatalysts. Therefore heterologous expression of such enzymes is extremely desired to design a cost effective and much safe bioconversion process. Heterologous expression of gene products in different expression system is sometimes limited by the presence of codons that are infrequently used in other organisms. Expression of such genes can be enhanced by systematic substitution of the endogenous codons with codons over represented in highly expressed prokaryotic genes. Redesigning a naturally occurring gene sequence by choosing different codons without necessarily altering the encoded amino acid sequence often dramatically increased protein expression levels. One disadvantage in biocatalyst used in production of low caloric sugar such as Psicose are the production cost of the enzyme due to low expression level of enzymes in native or heterologous organisms. In addition, due to the fact that the inter conversion between Fructose and Psicose is an equilibrium process, the large scale and high yield production of Psicose remains quite challenging.

Even though the enzymes are known that are capable of catalyzing the rare sugars but the gap still remain in mass production of enzymes and difficulties in their expression level besides the problems relating to the fact that the inter conversion between Fructose and Psicose is an equilibrium process.

It is understood that most of these enzymes do not get expressed at industrial scale to be used as a biocatalyst for bioconversion of sugars.

The inventors has identified the production constrain of ketohexose sugar which is a bottleneck for industrial scaling up and identified the expression level in heterologous is low for certain nucleotide which are less preferred. In order to overcome such problem, the nucleotide sequence obtained from *Pseudomonas cichorii* ST-24 which encodes for the enzymes responsible for bio-conversion were modified to increase the expression level substantially. Such modification resulted in better expression of the enzymes D-tagatose 3-epimerase of *Pseudomonas cichorii* and rhamnose isomerase of *Pseudomonas stutzeri* in *E. coli*. The *E. coli* host organism used in the invention is JM109 (a K-12 *E. coli* strain) was used for heterologous expression of recombinant D-tagatose 3-epimerase and rhamnose isomerase. It has been shown the *E. coli* K-12 cannot be converted into an epidemic pathogen by laboratory manipulation with r-DNA molecules and it will not colonize the human intestinal tract.

The present invention offers an alternative process for producing rare monosaccharides, in which the enzymes were expressed in *E. coli* at a higher level by modifying the gene sequence. In other words, the present research has made and effort to genetically modify the gene responsible for the production of enzymes, namely d-tagatose 3-epimerase to be used in bioconversion of fructose to psicose.

The genetic modification has resulted in increase in expression of protein in E. coli host.

SUMMARY OF THE INVENTION

Accordingly the present invention discloses a modified gene sequence encoding for D-tagatose 3-epimerase (DTEase) of *Pseudomonas cichorii* ST-24, responsible for conversion of Fructose in to Psicose and optimized expression of DTEase in *E. coli* for mass production of biocatalyst for bioconversion of sugars in an optimum conditions.

Further, the Psicose thus produced is further converted into Allose by using rhamnose isomerase. The nucleotide sequence is also modified to increase the expression of rhamnose isomerase.

The invention also discloses expression constructs comprising the modified genes to be expressed in *E. coli*.

The invention also relates to a process of producing psicose and allose from fructose using the recombinant enzymes obtained from modified gene.

Upon comparing with the expression level of the native D-tagatose 3-epimerase, it was found that the modification carried out in the native gene resulted in an increase in expression level in *E. coli* in the range of 14% to 18% of the total cellular protein. The gene construct carrying the modified gene in combination with highly inducible T7promoter instead of trc promoter is responsible for this better expression of intracellular D-tagatose 3-epimerase in *E. coli*.

The inventers also found consistent conversion of fructose in to psicose by immobilized recombinant DTEase in contact with up to 70% fructose in the reaction mixture. Moreover the 140 units of immobilized DTEase were able to achieve maximum conversion of fructose into psicose within 8 hrs at 50° C. (Table 3). In the prior art researcher had used 1000 to 3000 units of Dtase for the conversion of fructose to psicose. Moreover the time taken for the conversion was 30 to 90 hours (U.S. Pat. No. 5,679,562, U.S. Pat. No. 5,811, 271). For allose 100 units of immobilized rhamnose isomerase were able to achieve maximum conversion of fructose into psicose within 12 hrs (Table 4).

Upon comparing with the expression level of the native rhamnose isomerase, it was found that the modification carried out in the native gene resulted in an increase in expression level in *E. coli* in the range of 11% to 14% of the total cellular protein. The gene construct carrying the modified gene in combination with highly inducible T7 promoter instead of T5 promoter is responsible for this better expression of intracellular rhamnose isomerase in *E. coli*.

DETAILED DESCRIPTION OF THE INVENTION

The present invention discloses a modified gene sequence encoding for D-tagatose 3-epimerase (DTEase) of *Pseudomonas cichorii* ST-24, responsible for conversion of Fructose in to Psicose and optimized expression of DTEase in *E. coli* for mass production of biocatalyst for bioconversion of sugars in an optimum conditions. Further, the psicose thus produced is further converted into allose by using rhamnose isomerase. The nucleotide sequence is also modified to increase the expression of rhamnose isomerase. The invention also discloses expression constructs comprising the modified genes to be expressed in *E. coli*. The invention also relates to a process of producing psicose and allose from fructose using the modified gene.

Upon comparing with the expression level of the native D-tagatose 3-epimerase and rhamnose isomerase, it was found that the modification carried out in the native gene resulted in an increase in expression level in the range of 10% to 12% of the total cellular protein.

The present invention also discloses a novel and inventive protocol to assess the protein degradation and leaching during immobilization and bioconversion process using protein specific antibodies. Till date, no process has been shown to distinguish the whole length protein from degraded one. All available processes involve epitope tag to identify the whole length protein and therefore the degraded protein is not taken into consideration. For this process the recombinant proteins were expressed with 6×HIS epitope tag by using the pET23-DTE and pET23-RHI (FIGS. 1b and 2B) constructs and the recombinant proteins were purified by one step purification using an appropriate affinity matrix. The pure proteins were used as immunogen to generate polyclonal antibody in New Zealand white rabbits. The purified protein showed strong immunogenic response and anti sera were purified by affinity chromatography using Protein A-Sepharose 4B. Affinity purified antibody used in analytical process mentioned in the embodiment.

Gene encoding for D-Tagatose 3-epimerase (DTE) was modified for enhanced expression in *Escherichia coli* was synthesized using gene modification. The modified gene sequence is represented as SEQ ID NO 1. Similar modification was done to increase the expression of rhamnose isomerase in *E. coli* is represented as SEQ ID NO 2. Both sequence id nos 1 and 2 were cloned in to pET11 using NdeI and BamHI restriction enzyme site to generate pET11-DTE and pET-RHI constructs. Cloned gene sequences were confirmed by sequence analysis.

In a further aspect of the invention, a recombinant plasmid DNA (pET11-DTE) was transformed into *E. coli* expression host JM109 by electro transformation method to express D-tagatose 3-epimerase. A stable transformants were selected and deposited in international depository, namely MTCC bearing accession number MTCC5783.

In another embodiment of the invention, the large scale production of the above enzymes is disclosed. Importantly, the medium used for this purpose comprises no components of animal origin. The components of the medium were di-ammonium hydrogen phosphate, potassium dihydrogen phosphate and citric acid, which were sterilized in situ in the fermenter. Post sterilization a solution containing glucose, metal ions, trace elements and EDTA were added to the basal salt medium. Liquor ammonia was used as an alkali and nitrogen source. The temperature of the fermentation was maintained at 30 to 37° C. at a pH 5 to 8 and oxygen level was maintained not less than 40%, throughout the fermentation. The fermentation process at 2 L scale yields about 30 g/l biomass.

The organism containing the synthesized gene is able to produce more enzyme as a result of genetic modification of the native nucleic acid sequence of *Pseudomonas cichorii* ST-24 and *Pseudomonas stutzeri*. Besides the production of soluble enzyme, the inclusion bodies formed in the process is solubilized and refolded in vitro into active form using standard refolding conditions. In addition production of more soluble proteins in vivo were also achieved by co-expression of modified gene constructs (pET11-DTE and pET11-RHI) together with chaperone plasmids such as: pG-KJE8 or pGro7 or pKJE7 or pG-Tf2 or pTf16 (Takara).

Another aspect of the present invention is the immobilization of purified or partially purified enzymes in a suitable matrix known in the art for continuous operation.

In one more aspect of the invention relates to immobilization of the enzymes, namely, DTEase and RHIase using a suitable matrix. Partially purified or purified DTEase and RHIase were dialyzed against 20 mM Tris buffer (pH 8.0) for period in the range of 5 to 16 hours at temperature in the range of 1 to 4° C. followed by mixing with equal volume of 4% sodium alginate. The DTEase or RHIase containing sodium alginate solution was dropped by a surgical needle into chilled 0.2 M $CaCl_2$ solution with constant stirring. Immobilized bead was kept in $CaCl_2$ overnight at a temperature in the range of 4° to 10° C., followed by water wash and kept on a blotting paper for drying at 4° C. Protein retention was found to be about 85% w/v.

The optimization of process parameters for the production of Psicose was carried out with varying pH and temperature, which were used for the production of Psicose.

In one more feature of the invention is that the production of Psicose from Fructose was carried out by using 25 to 100 units of immobilized DTE enzymes with varying amount of Fructose as a substrate. The reaction was carried out with substrate concentration ranging from 10% to 90% at a temperature in the range of 20° to 80° C. and the pH in the range of 4.5 to 9.5. The conversion of Fructose to Psicose reached saturation at higher substrate concentration of more than 70% (w/w) at enzyme concentration of 100 to 200 Units preferably 120 to 150 units of enzyme with a reaction time of about 8 hrs.

The Psicose sugar solution was subjected to cation and anion exchange resins to remove salt and ions present in buffer solutions.

The sugar solution was concentrated using rotary vacuum evaporator system and subsequently passed through a column packed with activated charcoal, in order to remove the color. The purity was observed to be more than 90%.

Further, the Psicose thus produced is optionally converted into Allose by using enzyme rhamnose isomerase expressed in the same host used for the production of Psicose. The reaction of conversion of Psicose to Allose sugars is conducted with varied substrate loading from 10% to 90% at a temperature in the range of 10° to 70° C. and the pH in the range of 7 to 10.

In another aspect of the invention, the production of Allose from Psicose was carried out by using 25 to 100 units of immobilized RHIase. The sugar solution was subjected to cation and anion exchange resins to remove salt and ions present in buffer solutions. The Allose sugar solution was concentrated using rotary vacuum evaporator system and subsequently passed through a column packed with activated charcoal, in order to remove the color. The purity of the product was analyzed by HPLC and was found to be about 92%.

BRIEF DESCRIPTION OF THE DRAWINGS

FIG. 1: Schematic view of a gene construct generated for expression of D-tagatose 3-epimerase in *E. coli*

A: D-tagatose 3-epimerase encoding sequence (DTE) was cloned into pET11a using NdeI and BamHI sites. D-Tagatose 3-epimerase (DTE) gene is flanked by BglII, XbaI and NdeI at 5'end, and BamHI at 3'end. During cloning procedure NheI site was removed. The properties of plasmid are: T7 promoter, T7 terminator and Ampicillin resistance marker.

B: D-Tagatose 3-epimerase encoding sequence (DTE) was cloned into pET23a using BamHI and HindIII sites. D-Tagatose 3-epimerase (DTE) gene is flanked by BglII, XbaI, NdeI, NheI and BamHI at 5'end, and HindIII, NotI and XhoI at 3'end. During cloning procedure EcoRI, SacI and SalI sites were removed. The properties of plasmid are: T7 promoter, T7 terminator, Epitope tag: 6×HIS and Ampicillin resistance marker.

FIG. 2: Schematic view of a gene construct generated for expression of rhamnose isomerase in *E. coli*

A: Rhamnose isomerase encoding sequence (RHI) was cloned into pET11a using NdeI and BamHI sites. Rhamnose isomerase (RHI) gene is flanked by BglII, XbaI and NdeI at 5'end, and BamHI at 3'end. During cloning procedure NheI site was removed. The properties of plasmid are: T7 promoter, T7 terminator and Ampicillin resistance marker.

B: Rhamnose isomerase encoding sequence (RHI) was cloned into pET23a using BamHI and HindIII sites. Rhamnose isomerase (RHI) gene is flanked by BglII, XbaI, NdeI, NheI and BamHI at 5'end, and HindIII, NotI and XhoI at 3'end. During cloning procedure EcoRI, SacI and SalI sites were removed. The properties of plasmid are: T7 promoter, T7 terminator, Epitope tag: 6×HIS and Ampicillin resistance marker.

FIG. 3: Expression analysis of recombinant D-tagatose 3-epimerase in *E. coli*.

A. Control and recombinant *E. coli* cells [JM109 carrying pET11-DTE] were induced for protein expression by addition of 0.5 mM IPTG into media. Cells were lysed and supernatant and pellet fractions were subjected to 12% SDS-PAGE. Control strain: Lane 1 and 2 are uninduced and induced total cell lysate. Recombinant strain: Lane 3 and 4 are uninduced and induced total cell lysate. Cell fractions of recombinant strains: Lane 6 and 7 are uninduced cell supernatant and pellet, Lane 8 and 9 are two hrs induced supernatant and pellet, Lane 10 and 11 are four hrs induced supernatant and pellet. Abbreviations are: M: Protein molecular weight marker and kDa=Kilo Dalton.

B. Identity analysis of recombinant protein by Western blot analysis. Lane 1 and 2: Host cell lysate un-induced and induced. Lane 3 and 4: Recombinant strain uninduced and induced. Immuno-detection was carried our using protein specific antibodies.

FIG. 4: Expression analysis of recombinant rhamnose isomerase in *E. coli*.

A. Control and recombinant *E. coli* cells [JM109 carrying pET11-RHI] were induced for protein expression by addition of 0.2 mM IPTG into media. Cells were lysed and supernatant and pellet fractions were subjected to 10% SDS-PAGE. Control strain: Lane 1 and 2 are uninduced and induced total cell lysate. Recombinant strain: Lane 3 and 4 are uninduced and induced total cell lysate. Cell fractions of recombinant strains: Lane 6 and 7 are uninduced cell supernatant and pellet, Lane 8 and 9 are two hrs induced supernatant and pellet, Lane 10 and 11 are four hrs induced supernatant and pellet. Abbreviations are: M: Protein molecular weight marker and kDa=Kilo Dalton.

B. Identity analysis of recombinant protein by Western blot analysis. Lane 1 and 2: Host cell lysate un-induced and induced. Lane 3 and 4: Recombinant strain uninduced and induced. Immuno-detection was carried our using protein specific antibodies.

FIG. 5: HPLC analysis of recombinant D-tagatose 3-epimerase activity for substrate to product conversion.

The reaction mixtures were subjected to HPLC analysis to confirm the residual substrate and product formation. The product peaks (B) were confirmed with commercially available Fructose (Sigma Aldrich) (A) and Psicose as substrate and product standards, respectively.

FIG. 6: HPLC analysis of recombinant rhamnose isomerase activity for substrate to product conversion.

The reaction mixtures were subject to HPLC analysis to confirm the residual substrate and product formation. The product peaks (A) were confirmed with commercially available Psicose (Sigma Aldrich) (B) and Allose as substrate and product standards, respectively.

FIG. 7: Analysis of purified DTEase

A. Different fractions and purified protein were separated on 12% SDS-PAGE and stained by coomassie brilliant blue R250. Loading pattern are Lane 1: Marker; Lane 2: Total cell Lysate; Lane 3: Cell lyste before loading in column 1; Lane 4: Column 1 purified DTEase; Lane 5: Column 2 purified DTEase.

B. Identity analysis of recombinant protein by Western blot analysis. Lane 1 and 2: Host cell lysate un-induced and induced. Lane 3 and 4: Recombinant strain un-induced and induced. Immuno-detection was carried our using protein specific antibodies.

FIG. 8: Analysis of purified RHIase

A. Different fractions and purified protein were separated on 12% SDS-PAGE and stained by coomassie brilliant blue R250. Loading pattern are Lane 1: Marker; Lane 2: Total cell Lysate; Lane 3: Cell lyste before loading in column 1; Lane 4: Column 1 purified RHIase; Lane 5: Column 2 purified RHIase.

B. Identity analysis of recombinant protein by Western blot analysis. Lane 1 and 2: Host cell lysate un-induced and induced. Lane 3 and 4: Recombinant strain un-induced and induced. Immuno-detection was carried our using protein specific antibodies.

FIG. 9: Activity of a D-tagatose 3-epimerase against reaction pH and reaction temperature. The reaction mixture containing fructose and purified DTEase were incubated at different pH (A) and temperature (B) as indicated. After bioconversion the reaction was stopped by boiling the reaction mixture at 95° C. The reaction mixtures were subject to HPLC analysis to confirm the residual substrate and product formation with appropriate standards. The product peaks were confirmed with commercially available Fructose (Sigma Aldrich) and Psicose as substrate and product standards FIG. 10: Activity of a rhamnose isomerase against reaction pH and reaction temperature. The reaction mixture containing Psicose and purified RHIase were incubated at different pH (A) and temperature (B) as indicated. After bioconversion the reaction was stopped by boiling the reaction mixture at 95° C. The reaction mixtures were subject to HPLC analysis to confirm the residual substrate and product formation with appropriate standards. The product peaks were confirmed with commercially available Psicose (Sigma Aldrich) and allose as substrate and product standards FIG. 11: Sequence alignment analysis of modified gene sequence with native gene sequence encoding for D-tagatose 3-epimerase.

Modified gene sequence (represented as "modified") (SEQ ID NO: 1) was subjected to sequence alignment with native gene sequence (represented as "native") (SEQ ID NO: 3) of *Pseudomonas cichorii* ST-24 using multiple sequence alignment tool (ClustalW2). The nucleotides of modified gene sequence were marked as (.) and homology shared to native sequence was marked as (*). In the modified gene 22% of nucleotides were changed compared to native gene sequence.

FIG. 12: Sequence alignment analysis of modified gene sequence with native gene sequence encoding for rhamnose isomerase.

Modified gene sequence (represented as "modified") (SEQ ID NO: 2) was subjected to sequence alignment with native gene sequence (represented as "native") (SEQ ID NO: 4) of *Pseudomonas stutzeri* using multiple sequence alignment tool (ClustalW2). The nucleotides of modified gene sequence were marked as (.) and homology shared to native sequence was marked as (*). In the modified gene 23% of nucleotides were changed compared to native gene sequence.

EXAMPLES

The following examples are given by way of illustration, which should not be construed to limit the scope of the invention.

Example 1

Gene Construction

Gene encoding for D-Tagatose 3-epimerase (DTE) was modified for enhanced expression in *Escherichia coli* was synthesized using gene synthesis approach. The modified gene sequence is represented as SEQ ID NO 1. Similar modification was done to increase the expression of rhamnose isomerase in *E. coli* as represented in SEQ ID NO 2. Both sequence ID NOs 1 and 2 were cloned in to pUC57 using EcoRV restriction enzyme site to generate pUC57-DTE and pUC57-RHI constructs. Cloned gene sequence was confirmed by sequence analysis.

The DNA fragment encoding for D-tagatose 3-epimerase was PCR amplified using gene specific primers, and sub cloned into pET11a using NdeI and BamHI restriction enzyme sites to generate pET11-DTE (FIG. 1A). In addition the coding region was PCR amplified without stop codon using gene specific primers and sub cloned into *E. coli* expression vector pET23a (FIG. 1B) using BamHI and HindIII restriction enzymes to generate pET23-DTE-HIS construct expressing D-tagatose 3-epimerase with C-terminal 6×Histidine tag. The recombinant plasmid carrying D-tagatose 3-epimerase gene (pET11-DTE and pET23-DTE) was confirmed by restriction digestion analysis and followed by DNA sequencing.

The DNA fragment encoding for rhamnose isomerase was PCR amplified using gene specific primers, and sub cloned into pET11a using NdeI and BamHI restriction enzyme sites to generate pET11-RHI (FIG. 2A). In addition the coding region was PCR amplified without stop codon using gene specific primers and sub cloned into *E. coli* expression vector pET23a (FIG. 2B) using BamHI and HindIII restriction enzymes to generate pET15-RHI-HIS construct expressing rhamnose isomerase with C-terminal 6×Histidine tag. The recombinant plasmid carrying D-tagatose 3-epimerase gene (pET11-RHI and pET15-RHI) was confirmed by restriction digestion analysis and followed by DNA sequencing.

Example 2

Development of Recombinant *E. coli* with Gene Constructs For D-tagatose 3-epimerase Recombinant plasmid DNA (pET11-DTE) was transformed into *E. coli* expression host JM109 by electro transformation method and grown on Luria-Bertani (LB) agar plates containing ampicillin (50 g/ml). Individual colonies were picked and grown on LB liquid or defined media containing ampicillin (75 g/ml) for overnight at 37° C. Overnight culture was re-inoculated into 0.1 $OD_{600}$ in LB liquid or defined media without ampicillin and grown up to 0.6 OD$_{600}$ and the cells were induced for protein expression by addition of 0.5 mM of IPTG (Isopropyl β-D-1-thiogalactopyranoside) and incubated at 37° C. An aliquot of *E. coli* culture was collected at different time points. The cell lysate was subjected to SDS-PAGE and Western blot analysis to verify the protein expression (FIG. 3).

For Rhamnose Isomerase

Recombinant plasmid DNA (pET11-RHI) was transformed into *E. coli* expression host JM109 by electro transformation method and grown on Luria-Bertani (LB) agar plates containing ampicillin (50 g/ml). Individual colonies were picked and grown on LB liquid or defined media containing ampicillin (75 g/ml) for overnight at 37° C. Overnight culture was re-inoculated into 0.1 OD$_{600}$ in LB liquid or defined media without ampicillin and grown up to 0.6 OD$_{600}$ and the cells were induced for protein expression by addition of 0.5 mM of IPTG (Isopropyl β-D-1-thiogalactopyranoside) and incubated at 37° C. An aliquot of *E. coli* culture was collected at different time points. The cell lysate was subjected to SDS-PAGE and Western blot analysis to verify the protein expression (FIG. 4).

Example 3

Production of Enzymes, Namely, D-Tagatose 3-Epimerase and Rhamnose Isomerase

For large scale production of the above enzymes same protocols were followed. The medium used comprises no components of animal origin. The components of the medium were 4.0 g/L di-ammonium hydrogen phosphate, 13.3 g/L potassium dihydrogen phosphate and 1.7 g/L citric acid, 28 g/L glucose, 1.2 g/L MgSo4.7H2O, 45 mg/L Thiamine HCL, 1 g/L CoCl2.6H2O, 6 g/L MnCl2.4H2O, 0.9 g/L CuSo4.5H2O, 1.2 g/L H3BO3, 0.9 g/L NaMoO4, 13.52 g/L Zn (CH3COO—), 40 g/L Fe-Citrate and 14.1 g/L EDTA. Liquor ammonia was used as an alkali and nitrogen source. The temperature of the fermentation was maintained at 37° C. at a pH 6.9 and oxygen level was maintained not less than 40%, throughout the fermentation. The fermentation process at 2 L scale yields 30-14 g/l biomass.

Example 4

Purification of Enzymes

After completion of the fermentation the cells were centrifuged at 5000 g for 10 min and resuspend in 20 mM Tris-EDTA (TE) buffer, pH 8.0. The cells were lysed using the cell disruptor at 25 KPsi twice and the resulted cell lysate was clarified by centrifugation. The crude cell-free extract obtained from the supernatant following centrifugation at 27 000 g for 30 min at 4° C. was used for the purification. Clarified crude cell lysate was applied onto a Q-Sepharose column (GE, Healthcare) pre-equilibrated with 20 mM Tris-HCl buffer pH 8.0 and washed with five column volume of same buffer containing 100 mM NaCl. The bound proteins were eluted with NaCl gradient (0.1-0.4 M) in the same buffer, followed by step elution with 0.5 M and 1M NaCl wash in the same buffer. Fractions were collected and tested for D-tagatose 3-epimerase and rhamnose isomerase activity and purity by SDS-PAGE (FIGS. 7 and 8). The purification yield, activity recovery and fold purification for D-tagatose 3-epimerase and rhamose isomerase were shown in Table 1 and Table 2, respectively. Fractions containing the purified protein were dialyzed against 20 mM Tris pH 8.0 for 16 hours at 4° C. and concentrated by ultrafiltration using Centricon YM-10 devices (Millipore) prior to immobilization or stored with 20% glycerol at −20° C.

Example 5

Immobilization of Enzymes:

The same protocol was followed for DTEase and RHIase. Partially purified or purified DTEase and RHIase were dialyzed against 20 mM Tris buffer (pH 8.0) for 16 hours at 4° C. followed by mixing with equal volume of 4% sodium alginate (final concentration of sodium alginate was 2% w/v). The DTEase or RHIase containing sodium alginate solution was dropped by a surgical needle into chilled 0.2 M CaCl$_2$ solution with constant stirring. Immobilized beads were kept in CaCl$_2$ overnight at 4° C., followed by water wash and kept on a blotting paper for drying at 4° C. Protein retention was found to be 85% w/v with 2% w/v of sodium alginate.

Example 6

Production of Rare Monosaccharide
Production of Psicose by Recombinant DTEase

The optimization of process parameters for the production of Psicose was carried out with varying pH and temperature, which were used for the production of Psicose. Results are shown in FIG. 9.

Production of Psicose form Fructose was carried out by using 140 units of immobilized DTE enzymes with 100 g/l, 200 g/l and 400 g/l Fructose solution was used in 20 mM Tris buffer, 5 mM MnCl$_2$ (pH 8.0) at 50° C.

The sugar solution was subjected to cation and anion exchange resins to remove salt and ions present in buffer solutions.

The sugar solution was concentrated using rotary vacuum evaporator system and subsequently passed through a column packed with activated charcoal, in order to remove the color. The purity of the product was analyzed by HPLC (FIG. 5) and ions contaminations were analyzed in ion chromatography (Dionex). Physico-chemical properties and purity of the product were carried out using standard techniques to confirm the safety aspects of produced Allose in this process. Bioconversion of Psicose from Fructose was observed to be ~25%.

Production of Allose by Recombinant RHIase

The optimization of process parameters for the production of Allose was carried out with varying pH and temperature, which were used for the production Allose. Results are shown in FIG. 10.

Production of Allose from Psicose was carried out by using 25 units of immobilized RHIase with 15 g/l, 30 g/l and 60 g/l Psicose solution was used in 20 mM Tris buffer, 5 mM MnCl$_2$ (pH 8.0) at 60° C.

The sugar solution passed through cation and anion exchange resins to remove salt and ions present in buffer solutions.

The sugar solution was concentrated using rotary vacuum evaporator system and subsequently passed through a column packed with activated charcoal, in order to remove the color. The purity of the product was analyzed by HPLC (FIG. 6) and ions contaminations were analyzed in ion chromatography (Dionex). Physico-chemical properties and purity of the product were carried out using standard techniques to confirm the safety aspects of produced Psicose in this process. Bioconversion of Allose form Psicose was observed to be ~17%.

Advantage of the Present Invention:

The genetic modification of the native gene encoding for D-tagatose 3-epimerase and rhamose isomerase proposed by the present invention results into an increase in expression level in the range of 14% to 18% and 11% to 14% of the total cellular protein.

The recombinant enzymes thus produced by the claimed process appears to be active than the native one and the fact is established from the sugar conversion data. The present invention has used 140 units of Dtase for the conversion of fructose to psicose within a period of 8 hours. In the prior art researcher had used 1000 to 3000 units of Dtase for the conversion of fructose to psicose. Moreover the time taken for the conversion was 30 to 90 hours (U.S. Pat. No. 5,679,562, U.S. Pat. No. 5,811,271).

The invention claimed is:

1. A modified polynucleotide sequence comprising SEQ ID NO: 1 encoding D-tagatose 3-epimerase; or a modified polynucleotide sequence comprising SEQ ID NO: 2 encoding rhamnose isomerase.

2. The modified polynucleotide sequence according to claim 1 comprising SEQ ID NO: 2 encoding rhamnose isomerase.

3. The modified polynucleotide sequence according to claim 1 comprising SEQ ID NO: 1 encoding D-tagatose 3-epimerase.

4. The modified polynucleotide sequence according to claim 1 present in an expression construct.

5. The modified polynucleotide sequence according to claim 4, wherein SEQ ID NO: 1 and SEQ ID NO: 2 are operably linked to a T7 promoter.

6. The modified polynucleotide sequence according to claim 4, wherein the modified polynucleotide sequence encodes D tagatose 3-epimerase.

7. The modified polynucleotide sequence according to claim 4, wherein the modified polynucleotide sequence encodes rhamnose isomerase.

8. A host cell comprising the expression construct of claim 4.

9. The host cell of claim 8, wherein the host cell is a prokaryotic host cell.

10. A process of production of recombinant D-tagatose 3-epimerase or rhamnose isomerase, said process comprising the steps of:

1. culturing host cell transformed with an expression construct comprising SEQ ID NO: 1 or SEQ ID NO: 2 in a suitable medium in presence of IPTG or lactose for a period in the range of 2-3 hours,
2. isolation of expressed protein from the host cells by conventional method, and
3. purifying the recombinant proteins using chromatographic techniques.

11. The method according to claim 10, wherein the method is a method of producing D-tagatose 3-epimerase.

12. The method according to claim 10, wherein the method is a method of producing rhamnose isomerase.

13. A process of overproduction of rare monosaccharides from fructose, said process comprising the steps of:

1. culturing host cells transformed with an expression construct comprising SEQ ID NO 1: and SEQ ID NO: 2 in a separate suitable medium in presence of IPTG or lactose for a period in the range of 2-3 hours to produce D-tagatose 3-epimerase and rhamnose isomerase respectively,
2. isolating the expressed protein from the host cells by conventional method, and purifying the isolated protein using chromatographic techniques,
3. immobilizing D-tagatose 3-epimerase and rhamnose isomerase thus produced in the previous step in a suitable matrix,
4. contacting fructose with immobilized D-tagatose 3-epimerase for a period in the range of 5 to 10 hours to produce psicose, and 5. contacting D-psicose produced in the previous step with immobilized rhamnose isomerase for a period in the range of 6-12 hours to produce D-allose.

* * * * *